United States Patent [19]

Braun et al.

[11] Patent Number: 4,818,600
[45] Date of Patent: Apr. 4, 1989

[54] LATEX COATED BREATHABLE BARRIER

[75] Inventors: Ralph V. Braun, Roswell; Christine H. Brown, Dunwoody; Steven W. Fitting, Acworth; Lance J. Garrett, Jr., Marietta; David C. Law, Roswell; Robert E. Weber, Marietta, all of Ga.

[73] Assignee: Kimberly-Clark Corporation, Neenah, Wis.

[21] Appl. No.: 130,778

[22] Filed: Dec. 9, 1987

[51] Int. Cl.$^4$ .......................................... B32B 27/00
[52] U.S. Cl. ................... 428/290; 428/296; 428/334; 604/327; 604/328; 604/330; 604/335; 604/356; 604/358; 604/365; 604/366
[58] Field of Search ............ 428/296, 290, 334; 604/327, 328, 330, 335, 356, 358, 365, 366

[56] References Cited

U.S. PATENT DOCUMENTS

| | | | |
|---|---|---|---|
| 3,016,599 | 1/1962 | Perry, Jr. | 28/78 |
| 3,156,242 | 11/1964 | Crowe, Jr. et al. | 128/296 |
| 3,203,419 | 8/1965 | Joa | 128/290 |
| 3,215,580 | 11/1965 | Benning et al. | 156/332 |
| 3,252,848 | 5/1966 | Borsellino | 156/307 |
| 3,253,715 | 5/1966 | Painter et al. | 210/504 |
| 3,348,991 | 10/1967 | Abell et al. | 156/300 |
| 3,426,754 | 2/1969 | Bierenbaum et al. | 128/156 |
| 3,518,041 | 6/1970 | Brelich | 8/115.7 |
| 3,590,585 | 7/1971 | DeWinter | 61/36 |
| 3,597,307 | 8/1971 | Paulusma | 161/170 |
| 3,612,054 | 10/1971 | Matsuda et al. | 128/287 |
| 3,619,316 | 11/1971 | Ishida et al. | 156/77 |
| 3,622,422 | 11/1971 | Newman | 156/306 |
| 3,640,829 | 2/1972 | Elton | 161/159 |
| 3,660,200 | 5/1972 | Anderson et al. | 156/306 |
| 3,676,242 | 7/1972 | Prentice | 156/62.4 |
| 3,679,538 | 7/1972 | Druin et al. | 161/159 |
| 3,692,618 | 9/1972 | Dorschner et al. | 161/72 |
| 3,704,198 | 11/1972 | Prentice | 161/148 |
| 3,755,527 | 8/1973 | Keller et al. | 264/210 |
| 3,843,761 | 10/1974 | Bierenbaum et al. | 264/210 |
| 3,849,241 | 11/1974 | Butin et al. | 161/169 |
| 3,869,310 | 3/1975 | Fukushima et al. | 117/138.8 A |
| 3,870,593 | 3/1975 | Elton et al. | 161/159 |
| 3,891,487 | 6/1975 | Hoey | 156/78 |
| 3,916,447 | 11/1975 | Thompson | 2/46 |
| 3,932,682 | 1/1976 | Loft et al. | 428/296 |
| 4,006,052 | 2/1977 | Wang | 156/280 |
| 4,059,114 | 11/1977 | Richards | 128/287 |
| 4,100,324 | 7/1978 | Anderson et al. | 428/288 |
| 4,178,271 | 12/1979 | Busch et al. | 260/17 R |
| 4,196,245 | 4/1980 | Kitson et al. | 428/198 |
| 4,197,148 | 4/1980 | Shinomura | 156/79 |
| 4,197,371 | 4/1980 | Holst et al. | 521/84 |
| 4,226,906 | 10/1980 | Jacob | 428/283 |
| 4,240,416 | 12/1980 | Boich | 128/156 |
| 4,247,498 | 1/1981 | Castro | 264/41 |
| 4,257,997 | 3/1981 | Soehngen et al. | 264/145 |
| 4,289,832 | 9/1981 | Schwarz | 428/542 |
| 4,304,812 | 12/1981 | Perkins | 428/247 |
| 4,308,303 | 12/1981 | Mastroianni et al. | 428/90 |

(List continued on next page.)

FOREIGN PATENT DOCUMENTS

| | | |
|---|---|---|
| 0105629 | 4/1984 | European Pat. Off. |
| 0141592 | 5/1985 | European Pat. Off. |
| 0184392 | 6/1986 | European Pat. Off. |
| 3417909 | 11/1985 | Fed. Rep. of Germany. |
| 5626904 | 9/1972 | Japan. |
| 2103537 | 2/1983 | United Kingdom. |
| 2115702 | 9/1983 | United Kingdom. |

OTHER PUBLICATIONS

Kirk-Othmer—Encyclopedia of Chemical Technology 3rd edition, vol. 20—"Refactories to Silk"—pp. 207–230.
Kirk-Othemer—*Encyclopedia of Chemical Technology*3rd edition—vol. 23—"Thyroid & Anti-Thyroid Preparations to Vinyl Polymers"—pp. 848–865.
"Vinol Polyvinyl Alcohol Product Line".
Air Products & Chemicals Inc.—1977—"Air Products & Chemicals Inc. Technical Bulletin".

*Primary Examiner*—Marion C. McCamish
*Attorney, Agent, or Firm*—Patrick C. Wilson

[57] ABSTRACT

A breathable barrier which includes:

A. a first layer which is a porous sheet having a first side and a second side; and B. a second layer joined to the first side of the first layer, which second layer is a continuous film of a polymeric latex material, in which:

the film is not microporous in that it is substantially free of voids which connect the two surfaces of the film; and the film has an average thickness of from about 10 to about 250 microns;

wherein the first layer side of the second layer is intimately comingled with at least some of the fibers at the surface of the first side of the first layer, none of the pores at the surface of the first side of the first layer are so large as to significantly adversely affect the barrier properties of the breathable barrier as a consequence of the comingling, and the breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

In place of a coating, the continuous film can be a preformed film of a water-soluble polymeric material which is laminated to the porous sheet. In preferred embodiments, the porous sheet is a meltblown nonwoven web. The disclosed breathable barrier is especially useful as outer covers and baffles in such disposable absorbent articles as diapers, sanitary napkins, and incontinent pads. The breathable barrier also can be used in more durable or protective type applications including garments such as rainwear.

14 Claims, 6 Drawing Sheets

U.S. PATENT DOCUMENTS

| | | | |
|---|---|---|---|
| 4,323,534 | 4/1982 | DesMarais | 264/176 |
| 4,347,844 | 9/1982 | Ohki et al. | 128/287 |
| 4,356,229 | 10/1982 | Brodnyan et al. | 428/288 |
| 4,374,888 | 2/1983 | Bornslaeger | 428/198 |
| 4,377,615 | 3/1983 | Suzuki et al. | 428/213 |
| 4,379,192 | 4/1983 | Wahlquist et al. | 428/156 |
| 4,384,023 | 5/1983 | Okamura et al. | 428/338 |
| 4,386,131 | 5/1983 | Chauvel | 428/288 |
| 4,415,617 | 11/1983 | D'Elia | 428/86 |
| 4,430,278 | 2/1984 | Jones, Sr. | 264/22 |
| 4,443,511 | 4/1984 | Worden et al. | 428/198 |
| 4,452,845 | 6/1984 | Lloyd et al. | 428/220 |
| 4,454,191 | 6/1984 | Von Blucher et al. | 428/244 |
| 4,472,328 | 9/1984 | Sugimoto et al. | 264/41 |
| 4,504,978 | 3/1985 | Gregory, Jr. et al. | 2/59 |
| 4,508,113 | 4/1985 | Malaney | 128/132 |
| 4,519,909 | 5/1985 | Castro | 210/500.2 |
| 4,539,256 | 9/1985 | Shipman | 428/315.5 |
| 4,555,811 | 12/1985 | Shimalla | 2/51 |
| 4,560,611 | 12/1985 | Naka et al. | 428/266 |
| 4,563,229 | 1/1986 | Sorez | 156/64 |
| 4,578,069 | 3/1986 | Whitehead et al. | 604/370 |
| 4,588,457 | 5/1986 | Crenshaw et al. | 156/62.8 |
| 4,591,523 | 5/1986 | Thompson | 428/131 |
| 4,595,001 | 6/1198 | Potter et al. | 128/156 |
| 4,595,629 | 6/1986 | Mays | 428/286 |
| 4,603,077 | 7/1986 | Fujimoto et al. | 428/289 |
| 4,608,111 | 8/1986 | Hume III et al. | 156/306.6 |
| 4,610,915 | 9/1986 | Crenshaw et al. | 428/219 |
| 4,613,544 | 9/1986 | Burleigh | 428/315.5 |
| 4,622,259 | 11/1986 | McAmish et al. | 428/171 |

LATEX COATED BREATHABLE BARRIER

BACKGROUND OF THE INVENTION

The present invention relates to a breathable barrier, i.e., a structure which is substantially impervious to liquid water and other select aqueous solutions, but permeable by water vapor. More particularly, the present invention relates to a breathable barrier which is a porous sheet with a very well defined surface pore structure, such as a nonwoven web, coated with a very thin layer of latex or laminated to a latex film.

Absorbent articles, especially disposable absorbent articles such as diapers, sanitary napkins, bedpads, incontinent pads, nursing pads, and the like are well known and important items of commerce. Such articles are capable of absorbing and retaining liquid discharges from the body. They typically have an outer cover or baffle of a liquid-impermeable plastic film, such as a polyethylene or polypropylene film, to prevent retained liquid from leaking from the article and soiling items of clothing, bedding, furniture, and the like.

Such liquid-impermeable plastic film prevents, or at least minimizes, leakage by establishing a barrier to the passage of liquid from the absorbent article in situations where either the capacity of the absorbent article has been exceeded or the loading of the target zone has exceeded the capacity of the absorbent article to wick liquid from the target zone to storage areas.

Such plastic film, however, suffers from several disadvantages. Because the film is impermeable to both liquid and water vapor, the absorbent article feels hot when dry and clammy when wet. Such a clammy state can cause irritation of the skin and even severe dermatological problems, such as diaper rash on infants wearing disposable diapers which have been left on too long. In fact, diaper rash can develop relatively quickly because of illness or changes in diet. In addition, the plastic film employed as the outer cover or baffle is severely lacking in aesthetic qualities, especially for such products as disposable diapers.

One proposal for the elimination of such disadvantages is the use of a breathable, liquid impermeable barrier as the outer cover or baffle. As used herein, the term "breathable" means that the barrier is pervious to water vapor; that is, water vapor will pass through the barrier. While considerable progress has been made in the development of breathable films, such materials typically are lacking in aesthetic qualities.

Various breathable outer coverings or other materials are known. For example, U.S. Pat. No. 3,156,242 discloses a flexible absorbent sheet which is useful as a surgical dressing. The backing sheet or outer layer of the dressing is either air pervious by nature, such as a microporous film, or has had holes or slits formed in it. The example employed a perforated polyethylene film.

U.S. Pat. No. 3,426,754 teaches a breathable medical dressing. Such dressing comprises a backing having an open-celled structure, preferably coated with a continuous layer of a microporous pressure-sensitive adhesive. The backing employs a plastic film to which the desired properties have been imparted as a result of special processing conditions. The film typically can be prepared from polyolefins, polyacetals, polymethylene sulfide, polyethylene sulfide, polyphenylene oxide, polyamides, polyesters, and the like. The film possesses an open-celled structure, the voids of which are accessible to the outside surface by means of passageways which generally are under 5,000 Angstroms, e.g., from 100 to 5,000 Angstroms. In addition, such film has a final crystallinity of at least 40 percent.

A porous sheet and a process for making it are described in U.S. Pat. No. 4,347,844. The sheet is reported to be useful as a water-impermeable, vaporpermeable backing sheet for disposable diapers. The sheet contains a filler, the particles of which have been broken by the application of a compressive force to cause the formation of voids or spaces, i.e., micropores, which permit the passage of water vapor through the sheet while acting as a barrier to liquid water. The sheet apparently can be made of a nonfoamed thermoplastic resin, such as polyethylene and nylon. In addition, the patent suggests that the film can be a composite of a polyethylene or nylon film and spunbonded polyethylene or polyester. The use of a spunbonded material alone does not appear to be within the scope of the disclosure.

Another type of microporous film is described in U.K. Pat. No. GB 2,115,702B. The patent is directed toward an absorbent article, such as a disposable diaper or sanitary napkin, in which the article has a vapor-permeable, liquid-impermeable backing sheet. The backing sheet is composed of a film produced by mixing 100 parts by weight of a polyolefin resin, 28 to 200 parts by weight of a filler, and 10 to 70 parts by weight of a liquid or wax-like hydrocarbon polymer, molding the mixture to form a film, and then stretching the film laterally and/or longitudinally until it has a dimension of more than 1.2 times its original dimension in that direction, thereby resulting in the formation of fine pores in the film. Examples of polyolefins include polyethylene and polypropylene. A variety of fillers can be used, and examples of the hydrocarbon polymer include liquid polybutadienes, liquid polybutenes, and hydrogenates of liquid polybutadienes, among which saturated polyhydroxy-substituted hydrocarbons obtained by hydrogenating hydroxy-terminated liquid polybutadienes are preferred. See also U.S. Pat. No. 3,870,593 which describes stretching a film containing finely divided particles of a nonhygroscopic inorganic salt, such as calcium carbonate, in order to obtain a microporous film. The microporous sheet material descrbed in U.S. Pat. No. 3,640,829 also involves incorporating within the polymer an inorganic salt which is leached out to produce the micropores.

U.S. Pat. No. 4,591,523 relates to an apertured, macroscopically expanded, three-dimensional polymeric web exhibiting breathability and resistance to fluid transmission. The web is reported to have particular utility as a breathable barrier for a disposable diaper. The web preferably comprises a deeply drawn three-dimensional structure containing a multiplicity of debossments of macroscopic cross-section (i.e., visibly perceivable by the normal human eye at a perpendicular distance of about one foot), each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. These smaller apertures in each end wall are so spaced relative to all adjacent apertures in the end wall that the aqueous fluid menisci supported in the apertures do not contact one another.

Waterproof products capable of transmitting air and water vapor which have fabric-like aesthetic properties are described in U.S. Pat. No. 3,932,682. The products are made by spray-spinning filamentary material directly onto an open-celled microporous polymer film, such that thermal self-bonding occurs between the filamentary material and the film or by spray-spinning the filamentary material in the same manner onto an elastic film, stretching the resulting product until an open-celled structure is produced in the film portion of the product and thereafter heating or heat setting the resulting product at substantially constant length to impart dimensional stability thereto. Polymers suitable for making films appear to be those described in U.S. Pat. No. 3,426,754, discussed hereinabove. As already noted, the filamentary material is produced by spray-spinning, i.e., meltblowing, directly onto the film.

U.S. Pat. No. 4,308,303 describes a flocked, foam-coated, fibrous-reinforced, water vapor permeable barrier having the appearance of fabric and capable of filtering bacteria. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer. The film is rendered microporous by stretching a film which contains minute fracture sites or pore-nucleating agents such as finely divided filler and/or minute crystalline domains. The use of a finely divided, inorganic, water-insoluble, inert filler such as calcium carbonate having an average particle size of less than 3 microns is preferred.

U.S. Pat. No. 4,560,611 relates to a moisture-permeable, waterproof coated fabric. Briefly, a microporous polyurethane layer is formed on a base fabric which may be knitted, woven, nonwoven, or the like. The coating solution consists of a polar organic solvent solution containing 8 to 25 percent by weight of a polyurethane elastomer, 0.1 to 10 percent by weight of a water repellent agent, 0.2 to 3 percent by weight of a polyisocyanate, and 1 to 8 percent by weight of a nonionic surfactant. The water repellent agent typically is a fluorine- or silicone-based material. The polyisocyanate usually will be any of the well known di- or triisocyanates. The polyurethane elastomer can be a polyester or polyether polyurethane.

A somewhat similar approach is described in European patent application No. 85308671.8, Publication No. 0 184 392 A2. A waterproof, moisture-vapor permeable unitary sheet material comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough, thereby rendering the sheet material breathable. Preferably, the average pore size will be less than about 10 percent of the thickness of the matrix. By way of example, the average pore size for a matrix having a thickness of about 10 to 50 micrometers typically will be on the order of 1 to 5 micrometers or less. By contrast, the average pore size or opening of a woven fabric is about the same magnitude as its thickness. A matrix having too large a pore size will permit the passage of water therethrough as hydrophilic material solidified therein will not sufficiently close the pores against the passage of liquid. The matrix can be prepared by known methods from any polymeric material which is substantially impenetrable by water. Suitable polymeric materials include polyolefins, polyesters, polyamides, and the like. The preferred hydrophilic material is polyethylene oxide which preferably is polymerized with a polyisocyanate to give a polyurethane.

U.S. Pat. No. 4,197,371 discloses a water vapor absorbing and transmitting sheet material. The sheet material comprises a natural or synthetic rubber or a rubber-like polymer having uniformly incorporated therein particles of at least one swellable modified polymer. Examples of suitable swellable modified polymers include, among others, modified starches and celluloses. Apparently, such sheet materials are not suitable for use as an outer cover for a disposable absorbent product, e.g., a diaper or sanitary napkin. See also U.S. Pat. No. 4,178,271 which describes a similar sheet material based on a sheet-like structure of poly(vinyl chloride) or a copolymer of vinyl chloride.

U.S. Pat. No. 3,869,310 describes flexible sheet materials which are leather-like. Although the materials allegedly have improved physical properties, particular properties, such as water vapor permeability, are not discussed. The materials comprise a nonwoven fibrous mat and a polymeric impregnant which has a porous structure and is substantially not bonded to the fibers of the mat. The materials are obtained by preparing a nonwoven fibrous mat composed of fibers prepared from at least two different polymeric materials, impregnating the mat with a first liquid which is a solvent for one of the polymeric materials and a nonsolvent for the other polymeric materials, dissolving the fibers composed of the polymeric material which is soluble in the liquid, and coagulating the polymer solution resulting from the addition of the first liquid into a porous polymeric structure which is substantially not bonded to the undissolved fibers by the addition of a second liquid which is a nonsolvent for all of the polymeric materials originally present in the nonwoven fibrous mat but which is at least partially miscible with the first liquid. The list of suitable polymeric materials which can be employed includes poly(vinyl alcohol), although the preferred combinations of polymeric materials apparently are nylon-6 and polystyrene, nylon-6 and polypropylene, poly(ethylene terephthalate) and polystyrene, poly(vinyl chloride) and polypropylene, nylon-6 and poly(vinyl acetate), and nylon-6 and a polyurethane elastomer. One example, however, involved the use of a nonwoven mat composed of fibers of poly(vinyl chloride) and poly(vinyl alcohol); the first liquid was N,N-dimethylformamide which is a solvent for poly(vinyl alcohol) but a nonsolvent for poly(vinyl chloride).

The use of poly(vinyl alcohol) as a binder for a nonwoven fabric is described in U.S. Pat. No. 3,518,041. The nonwoven fabric is composed of cellulosic fibers alone or in combination with other natural or synthetic fibers. The binder is a poly(vinyl alcohol) resin in film, powder, fiber, or other particulate form which is crosslinked in situ with formaldehyde. The binder is applied to the fabric as an aqueous solution or poly(vinyl alcohol) fibers may be incorporated into the fabric and activated by treating the fabric with water. The fabric then is treated with an aqueous solution of formaldehyde which contains a catalyst.

A disclosure somewhat similar to that of the above patent is found in U.S. Pat. No. 3,253,715 which describes boil-proof nonwoven filter media. The media are prepared by treating a multilayered nonwoven fabric with a binder which is an aqueous solution of poly(vinyl alcohol) and a polyacrylic acid or crosslinked polyacrylic acid.

It is interesting to note that, in contrast to U.S. Pat. Nos. 3,518,041 and 3,253,715, U.S. Pat. No. 3,590,585 describes a composite structure, useful as an artificial seaweed, which employs water-decomposable poly(vinyl alcohol) filaments to temporarily hold buoyant, water-resistant strands in place during handling, transporting, and installing of the product. Also of interest in this regard is U.S. Pat. No. 4,304,812 which describes the backcoating of an open-weave fabric. Prior to the backcoating step, a temporary protective coating is applied to the face of the fabric. After backcoating the fabric, the protective coating is removed with a solvent medium. Suitable protective coatings preferably are at least partially water soluble and include water-soluble poly(vinyl alcohol) or partially hydrolyzed poly(vinyl acetate).

U.S. Pat. No. 3,597,307 describes a supple sheet material which is composed of a fibrous nonwoven web and a polyurethane filler. The fibers of the web can be prepared from poly(vinyl alcohol) and the amount of the filler can be up to 30 percent by weight, based on the weight of the sheet material. Although the sheet material is stated to have a good water vapor pick-up value, it is not known if the material is permeable to water vapor. See also U.S. Pat. No. 4,006,052.

U.S. Pat. No. 3,891,487 discloses a decorative laminate which has a textile backing, a crushed, thermoset plastic foam bonded thereto, and a transparent polymeric film overlaying the foam. The film preferably is cast from a latex; suitable materials for preparing the latex include poly(vinyl alcohol). The film can be made breathable by mechanically foaming the latex before casting, mechanically puncturing the film, using chemical blowing agents, or dissolving or digesting out temporary fillers placed in the latex before it is cast. The textile backing apparently can be either woven or nonwoven. The decorative laminate is useful as, for example, a simulated oil painting, and clearly is not intended to be contacted by water.

Microporous coated fabrics are described in U.S. Pat. No. 4,226,906. Microporosity apparently results from the use of clustered microspheres. The microspheres may be synthetic or naturally occurring. If the former, they are prepared by bonding individual microspheres in a matrix which is insoluble in the coating composition; the bonding agent for such matrix can be, for example, poly(vinyl alcohol). However, the patent does not appear to teach the use of poly(vinyl alcohol) in the preparation of microporous coated fabrics when naturally occurring microspheres are used; in such case, the coating composition was based on poly(vinyl chloride) and the fabric was a nonwoven polyester.

U.S. Pat. No. 4,415,617 discloses a base fabric for the manufacture of embroidery and lace. The base fabric is a nonwoven web of poly(vinyl alcohol) fibers which has been processed in such a manner as to convert one surface of the web into a gas-permeable film comprising thermoplasticized and rehardened, flattened fibers and portions of fibers. The base fabric then can be dissolved away from embroidery stitched thereon by exposing the fabric to water at a temperature of about 100° C.

U.S. Pat. No. 4,454,191 describes a waterproof and moisture conducting fabric coated with a hydrophilic polymer. The fabric can be a woven, knit, felt, or nonwoven material which is composed of natural, synthetic, or mineral fibers. The fabric itself must be permeable to water vapor. The fabric is sealed with a hydrophilic polymer which is capable of absorbing, transporting, and releasing water molecules. Such capability results from the presence in the polymer of hydrophilic groups, such as hydroxy, amino, ether, and carboxy groups. Thus, suitable polymers include those prepared from hydroxyalkyl acrylates, the acrylic or methacrylic esters of polyalkylene oxides or polyalkylenimides, and the like. Other suitable polymers include modified vinyl alcohol resins, regenerated cellulose, a poly(vinyl chloride) having built-in monomers which have powerful hydrophilic groups, copolymerizates of vinyl chloride and vinyl acetate in which the acetate groups have been hydrolyzed to hydroxy groups, and polyurethanes having excess hydroxy or amino groups.

A somewhat related disclosure is found in German Published patent application No. 3417909 A1, which describes the use of a water-soluble poly(vinyl alcohol) film in the resorbent material of a sanitary pad. The film reportedly prevents soiling of clothing while permitting sanitary disposal of the used article. There appears to be no mention of the characteristics of the film or where and how the film is placed in the pad.

It perhaps should be mentioned that there is a relatively large body of literature on the preparation of microporous films, only a relatively small portion of which has been discussed hereinabove. While a detailed discussion of such body of literature is beyond the scope of this section, a limited number of additional, representative references perhaps should be mentioned for the sake of completeness. Such references include, by way of illustration only, U.S. Pat. Nos. 4,247,498, 4,519,909, 4,257,997, 4,452,845, 4,539,256, 3,843,761, 3,679,538, 4,430,278, 4,289,832, 4,384,023, 4,472,328, 4,197,148, U.K. Published patent application No. GB 2,103,537A, Japanese Published patent application No. 57-142323, and European patent application No. 84307198.6, Publication No. 0 141 592 A2, and 83305161.8, Publication No. 0 105 629 A2.

Although various of the breathable barriers described above have proven useful in such absorbent articles as disposable diapers and sanitary napkins, there still is a need for an effective breathable outer cover or baffle which has a clothlike feel and can be manufactured cheaply in large quantities.

Absorbent articles such as diapers, sanitary napkins, nursing pads, and incontinent products are generally classified as single use disposable items. While these items have a need for a breathable barrier material, this same need extends into more durable products such as rainwear and other applications where a more cloth-like water impermeable/ water vapor permeable material is required.

SUMMARY OF THE INVENTION

It therefore is an object of the present invention to provide a breathable barrier.

Another object of the present invention is to provide a breathable barrier which is suitable for use as an outer cover or baffle for a disposable absorbent article.

Yet another object of the present invention is to provide a breathable barrier which is suitable for semi-durable and durable applications such as waterproof garments including rainwear.

A further object of the present invention is to provide a breathable barrier which is clothlike in appearance and feel.

These and other objects will be apparent to one having ordinary skill in the art from a reading of the specification and claims which follow.

Accordingly, the present invention provides a breathable barrier which comprises:

A. a first layer which is a porous sheet having a first side and a second side; and
B. a second layer joined to said first side of said first layer, which second layer comprises a continuous film of a latex material, in which:

said film is not microporous in that it is substantially free of voids which connect the two surfaces of said film;
water molecules are capable of being transported through the thickness of said film; and
said film has an average thickness of from about 10 to about 250 microns;

wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

The present invention also provides a breathable barrier which comprises a porous sheet laminated on at least one side to a film of a latex material, in which:

said film is not microporous in that it is substantially free of voids which connect the two surfaces of said film;
water molecules are capable of being transported through the thickness of said film; and
said film has an average thickness of from about 10 to about 250 microns;

wherein said breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

The present invention still further provides a breathable barrier which comprises:

A. a first layer which is a porous sheet having a first side and a second side; and
B. a second layer joined to said first side of said first layer, which second layer comprises a continuous film of a latex, in which:

said film is not microporous in that it is substantially free of voids which connect the two surfaces of said film; and
said film has an average thickness of from about 10 to about 250 microns;

wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

The present invention yet further provides a breathable barrier which comprises a porous sheet laminated on at least one side to a film of a latex, in which:

said film is not microporous in that it is substantially free of voids which connect the two surfaces of said film; and
said film has an average thickness of from about 10 to about 250 microns;

wherein said breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

In preferred embodiments, the porous sheet or first layer is a nonwoven web. In other preferred embodiments, the porous sheet is a meltblown or spunbonded web. In still other preferred embodiments, the porous sheet is a meltblown or spunbonded web which is composed of polyolefin fibers, e.g., polyethylene or polypropylene fibers.

The present invention additionally provides a multilayer absorbent article in which at least one layer is a breathable barrier as described and claimed herein.

In preferred embodiments, the absorbent article is a disposable diaper, a sanitary napkin, an incontinent pad, a nursing pad or rainwear.

DETAILED DESCRIPTION OF THE INVENTION

Figure 1:
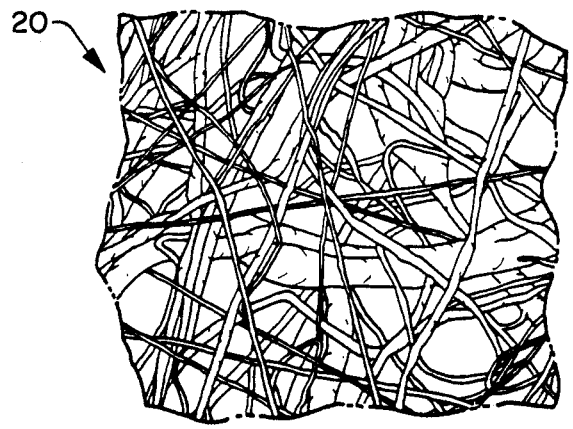
FIG. 1 is a magnified representation of a plane view of a polypropylene meltblown nonwoven web.
Figure 2:
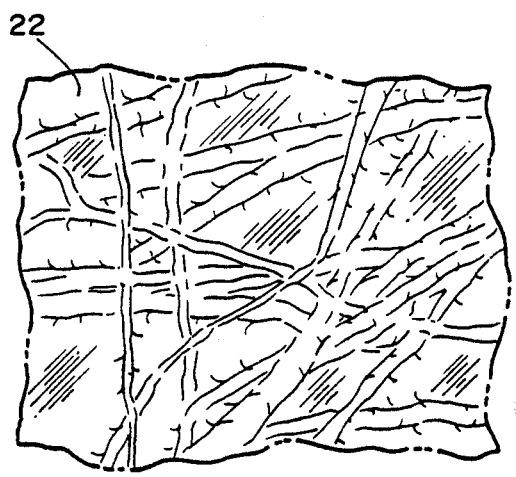
FIG. 2 is a magnified representation of a plane view of a polypropylene meltblown nonwoven web coated in accordance with the present invention, taken of the coated side.

As used herein, the term "breathable barrier" means a material which is permeable to water vapor as measured by the water vapor transmission rate at 37° C. and about 50 percent relative humidity, but which is impermeable to 0.9 percent by weight of saline solution at about 21° C. for a period of at least about one hour at a hydrostatic head of at least about 11.4 cm. The material is permeable to water vapor for the purposes of the present invention if it has a water vapor transmission rate at 37° C. and about 50 percent relative humidity of from about 100 to about 2,200 g/m$^2$/24 hours.

As a matter of convenience, the terms "porous sheet" and "first layer" are used interchangeably throughout this specification, with occasional cross-referencing. The same is true of the terms "continuous film" or "film" or variations thereof and "second layer."

In the broadest interpretation of the present invention, the porous sheet or first layer can be any porous material which is desired to be converted to a breathable barrier. Thus, such porous sheet can be a paper substrate, woven web, knitted fabric, spunlaced material, bonded carded web, needle punched material, stitch bonded fabric, meltblown web, spunbonded web, coformed web, or the like. Preferably, however, the porous sheet will be a nonwoven web. Most preferably, the porous sheet will be a spunbonded, meltblown, or coformed nonwoven web. The critical property of the material chosen for the first layer is that the surface which is coated with latex has a pore structure which is small enough to allow the latex coating to bridge the pores and not create holes or gaps which would jeopardize the liquid impermeable nature of the breathable barrier. As can be seen from FIGS. 1 through 6 and in particular the cross-sectional scanning electron micrograph of FIG. 5, the pore structure should be small enough that the latex coating virtually sits on top of the porous sheet with very little or no penetration into the fibrous structure.

Various methods for making porous sheets are, of course, well known to those having ordinary skill in the art and need not be discussed herein. For the most preferred porous sheets, however, representative methods are described in, for example, U.S. Pat. Nos. 3,016,599, 3,755,527, 3,704,198, 3,849,241, and 4,100,324, and 3,692,618, all of which are incorporated herein by reference. With respect to coformed webs, it perhaps should be noted that the web in general will consist of primary web-forming fibers with secondary fibers or particles dispersed therein.

The material from which the porous sheet is prepared is not known to be critical, provided that there is sufficient adhesion between the porous sheet and the polymeric latex material. That is, the second layer must be joined to the first layer. Moreover, it should be appreciated by one having ordinary skill in the art that the levels of adhesion for any given porous sheet may differ, depending upon the nature of the polymeric latex material and whether it is applied as a solution or as a preformed film. Although the use of a supplemental adhesive, i.e., an adhesive material different from latex, is contemplated and comes within the scope of the present invention, such use is not preferred. In any case, whether or not adhesion is sufficient for any given combination of porous sheet material and polymeric latex material is readily determined by one having ordinary skill in the art without a need for undue experimentation. Moreover, when insufficient adhesion is observed, one having ordinary skill in the art, following the guidelines contained herein, can easily determine conditions under which sufficient adhesion will be achieved.

When the porous sheet is a nonwoven web, the preferred materials for the preparation of the web are polyolefins. For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block copolymers of two or more polyolefins (or two or more different polyolefin monomeric precursors) or of one or more polyolefins and one or more nonpolyolefin polymers. Similarly, polymer blends can utilize two or more polyolefins or one or more nonpolyolefin polymers. As a practical matter, homopolymers and copolymers and polymer blends involving only polyolefins are preferred, with homopolymers being most preferred.

Examples of polyolefins and other suitable web materials include polyethylene, polystyrene, poly(vinyl chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

The size and thickness of the porous sheet are not critical. However, those having ordinary skill in the art should appreciate that it may be necessary to alter film thicknesses or materials if very thin or very thick porous sheets are employed. The present invention is unique in part because it permits the use of relatively thin films or second layers without sacrificing barrier properties. Thus, one goal of the present invention is to keep the films relatively thin, which in turn imparts a more cloth-like feel and appearance to the material. Consequently, some experimentation may be required to optimize the performance of the resulting breathable barrier upon changing the thickness of the porous sheet or first layer. In addition, some porous sheets, most notably meltblown webs, may exhibit partial barrier characteristics to liquid water and other aqueous solutions, which characteristics should be taken into consideration when planning film thicknesses. In fact, the presence of such characteristics in the first layer is both desirable and preferred. Again, however, the key to keeping the latex layer thin is to use a porous sheet with very small pore diameter, at least at the surface of the porous sheet which is to be coated with the latex material.

By way of illustration, satisfactory breathable barriers have been prepared using nonwoven spunbonded or meltblown porous sheets as first layers. Spunbonded basis weights have varied from about 13.6 to about 102 g per square meter, or g/m², and meltblown basis weights have varied from about 3.4 to about 102 g/m².

As already stated, the second layer is a continuous film of a polymeric latex material. Such film can be a preformed film which is joined or laminated to the porous sheet or first layer by any suitable method known by those having ordinary skill in the art, such as thermal bonding, chemical or adhesive bonding, solvent bonding, ultrasonic bonding, and the like. Of course, the joining method should not significantly adversely affect the barrier properties of either the film or the porous sheet. Alternatively, and preferably, the second layer of continuous film can be formed in situ from an aqueous coating on the porous sheet or first layer. Because the in situ formation of the second layer is preferred, most of the discussion which follows is directed thereto.

When the continuous film or second layer is formed in situ on the porous sheet or first layer, the structure of the porous sheet, e.g., the sizes of the pores at the surface of the porous sheet on which the film will be formed, is of concern in the sense that none of such pores can be so large as to interfere with the formation of the continuous film in such a manner as to significantly adversely affect the barrier properties of the breathable barrier. It is important to note that perfection is not required; it is necessary only that those film imperfections which are present do not result in a significant deterioration of the barrier properties, especially with respect to liquid water or other aqueous based liquids such as blood and urine.

In the case of the most preferred porous sheet, i.e., a meltblown web, it is estimated that, in order to obtain generally satisfactory barrier properties, each of at least about 50 percent of the pores at the surface to be coated of the meltblown porous sheet should have a cross-sectional area of less than about $3.2 \times 10^{-8}$ m², with none of the pores being so large as to prevent the formation of the continuous film in such a manner as to significantly adversely affect the barrier properties of the breathable barrier. By significantly adversely affecting the barrier properties, it is meant that the material is impermeable to 0.9 percent by weight of saline solution at 21° C. for a period of at least about one hour at a hydrostatic head of at least about 11.4 cm. Moreover, it is believed that optimum barrier properties should be possible with meltblown webs when essentially none of the pores at such surface has a cross-sectional area in excess of about $3.2 \times 10^{-8}$ m². Because of the numerous combinations of porous sheets and coatings, however, it is not feasible to do more than offer the foregoing guidelines with respect to the pore size distribution of the porous sheet.

When the polymeric latex material is applied to the porous sheet as an aqueous coating to form a continuous film in situ, it must, of course, be capable of forming a continuous film under the conditions of application. In general, the polymeric latex material can be any polymeric latex material with or without other additives which, in addition to the foregoing requirement, will form a film which:

is not microporous in that it is substantially free of voids which connect the two surfaces of the film;
is capable of transporting water molecules through the thickness of the film; and
has an average thickness of from about 10 to about 250 microns.

These film characteristics also apply to the preformed film which is laminated to the porous sheet.

As already noted, the average thickness of the second layer should be in the range of from about 10 to about 250 microns. Preferably, the average thickness of the second layer will be in the range of from about 10 to about 100 microns, more preferably from about 10 to about 50 microns, and most preferably from about 12 to about 25 microns.

Figure 3:
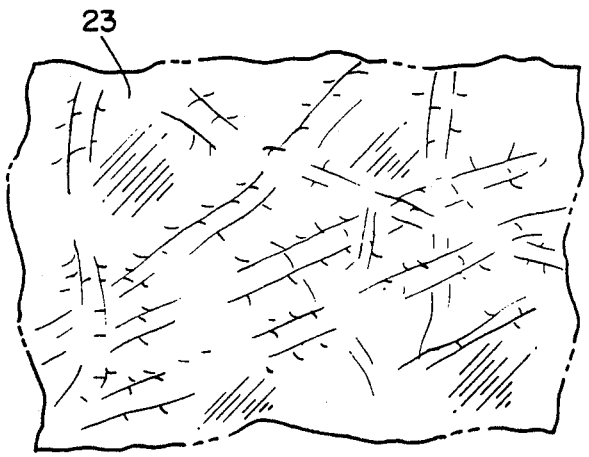
FIG. 3 is a magnified representation of a plane view of a polypropylene meltblown nonwoven web coated twice on the same side in accordance with the present invention in which the coating is latex.

Referring to FIG. 1, there is shown a magnified representation of a meltblown polypropylene nonwoven web 20 which comprises the first layer to which the coating/film of polymeric latex material is applied. As described previously, it is desirable to have the pores at the surface of the meltblown web which is to be coated to be as small as possible in order to support the latex coating. As a result, in a preferred embodiment at least about 50% of the pores at the surface of the meltblown web should have a cross-sectional area of less than about $3.2 \times 10^{-8}$ m². The polymeric latex material may be applied to the surface of the meltblown web as a single coat 22 (FIG. 2) or in two or more separate coats 23 (FIG. 3).

Figure 4:
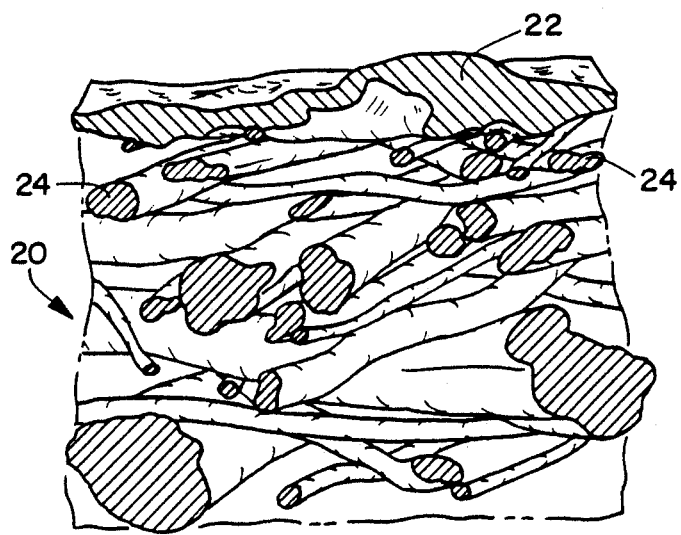
FIG. 4 is a magnified representation of a cross-sectional view of a polypropylene meltblown nonwoven web coated with latex in accordance with the present invention.

Referring to FIG. 4, once applied, the latex coating or film 22 adheres to the uppermost fibers 24 of meltblown layer 20 thereby forming the breathable barrier material of the present invention.

Figure 5:
FIG. 5 is cross-sectional view scanning electron micrograph of a 0.5 oz/yd$^2$ meltblown layer bonded to a 0.7 oz/yd$^2$ spunbond layer with the meltblown layer coated with 0.7 oz/yd$^2$ of latex in accordance with the present invention taken at a magnification of 100×.
Figure 6:
FIG. 6 is a plane view of the surface of the latex coating of FIG. 5 in accordance with the present invention taken at a magnification of 100×.

It has been found that meltblown materials are particularly well suited as the porous sheet material due to their fine denier and pore size which allows the polymeric latex coating to coat the outermost surface of the web and bridge the open pores of the porous sheet material. Due to the inherent characteristics of meltblown materials, a latex coated meltblown composite may not have sufficient strength and integrity for certain end-use applications. As a result, it may be desirable to bond the meltblown nonwoven web to a secondary material such as a spunbond material to increase the overall integrity and strength of the breathable barrier material. Such a composite is shown in the scanning electron micrographs of FIGS. 5 and 6. Referring to FIG. 5, the latex coating is supported and adheres to the surface of the fine fiber meltblown material which is in turn supported and bonded to the stronger spunbond layer. Referring to FIG. 6, the fine fiber, small pore meltblown material permits the application of a thin coat of polymeric latex material to the web with a relatively high degree of uniformity. As a result, the size and number of holes, if any, in the latex coating are kept to a minimum.

If a third layer is present which also is a continuous film of a polymeric latex material, and the third layer is joined to the second layer, then both the second and third layer thicknesses can be reduced. Under these conditions, the preferred range for the thicknesses of each such layer is from about 1.5 to about 85 microns, with a range of from about 1.5 to about 12 microns being more preferred. The most preferred thickness range for each of the two adjacent film layers is from about 1.5 to about 10 microns.

It should be noted that average film thickness is involved, not maximum film thickness. Because of the inherent relative roughness of the surfaces of many porous sheets, and nonwoven webs in particular, film thickness typically varies over the area constituting the second layer. This necessitates dealing with average film thickness. Moreover, the average film thickness is an adequate measure of the amount of the continuous film which constitutes the second layer. Stated differently, some variability or imprecision in film thickness is acceptable since the barrier properties of the film do not appear to be extremely sensitive to film thickness above a certain minimum. Note, however, that the latex film thickness does have a very dramatic impact upon the breathability/vapor permeability of the overall material. Breathability and liquid impermeability are inversely related. As the film thickness increases, the breathability of the material rapidly decreases. As a result, to maximize breathability, the film thickness should be as small as possible without sacrificing barrier and durability properties. An upper limit on the latex film thickness is approximately 250 microns. Beyond this limit the barrier material begins to lose its cloth-like appearance and the breathability of the material suffers.

A related problem is the difficulty of accurately measuring film thickness, unless the film is preformed. For the purposes of the present invention, it is sufficient if film thickness is only estimated. A reasonable estimate of the thickness of a film can be made from the amount of add-on of the latex composition if the density composition is known. With the latex coatings employed in the examples, it was found that each $g/m^2$ of add-on was approximately equivalent to 0.85 micron of film thickness.

In general, the polymeric latex materials suitable for use in the present invention can be either natural or synthetic, and the former group of materials can be modified, if desired, to achieve particular properties. The natural and modified natural materials included, by way of illustration only, Rohm and Hass Rhoplex ® E-940, Rhoplex ® NW-1715, Rhoplex ® E-1847 and B. F. Goodrich Elastoplast ® V-29.

In many cases, it may be necessary to include a crosslinking agent in order to obtain the requisite film properties. However, suitable crosslinking agents and their uses are well known to those having ordinary skill in the art. Suitable crosslinking agents are those known in the art, such as glyoxal; formaldehyde; urea-formaldehydes; melamine-formaldehydes; metal-ion complexes, such as zinc or zicronium ammonium carbonate; polyvalent melt salts, such as zinc or magnesium oxide; tri-functional aziridine derivatives; metal compounds, such as cupric ammonium complexes; chromium complexes, organic titanates, and dichromates; and the like. When required, a crosslinking agent usually is employed in an amount in the range of from about 1 to about 5 percent by weight, based on the weight of latex in the aqueous solution, although higher or lower amounts can be employed if desired.

In addition to the use of chemical crosslinking agents as discussed above, the formed latex film can be crosslinked by radiation, such as electron beam radiation, ultraviolet radiation, and the like. The formed latex film also can be crosslinked either thermally or by pH activation by heating the film to dryness or to an elevated temperature with a preferred temperature range from about 130° to 150° C. The crosslinking time can vary from a few seconds to a few minutes. Thermal crosslinking is preferred over the inclusion of a chemical crosslinking agent in the coating solution, especially when the breathable barrier is to be used in a disposable absorbent article such as a diaper or sanitary napkin.

As indicated hereinbefore, the polymeric latex material preferably is applied to the porous sheet as an aqueous solution. Application usually is made at ambient temperature and pressure, although such conditions are not mandatory. Indeed, any combination of temperature and pressure can be employed, although for reasons of economics and convenience, ambient temperature and pressure are preferred. The concentration of polymeric latex material in the solution is not known to be critical and usually is a matter of convenience. In practice, solid concentrations of from about 30 to about 45 percent by weight are typical. The preferred concentration range is from about 20 to about 45 percent by weight as employed in the examples. The advantage of higher solids content is that there is less liquid to drive off during the drying of the coating.

The method of application is not known to be critical and largely is a matter of convenience. Thus, the latex solution can be applied by spraying, dipping, brushing, doctor blade, roller, Meyer rod, and the like. In addition, a single coat or multiple coats can be applied. Moreover, if multiple coats are applied, the application solution does not have to be the same for each application. The several solutions can utilize different concentrations of latex, the presence or absence of such compounds as crosslinking agents and plasticizers, different polymeric materials at the same or different concentrations, or combinations of any of the foregoing variations.

After the aqueous solution of latex polymeric material has been applied to the porous sheet, the sheet is dried by removing water, preferable at an elevated temperature. The removal of water generally results in the formation of a film of the polymeric latex material. If a subsequent porous sheet is to be applied adjacent to the film, such application can be done before drying has been completed and is preferred in cases where the polymeric latex material has adhesive properties. If desired, multiple coatings of the polymeric latex material solution can be applied, with the last-applied coating serving as the adhesive layer, especially when additional layers of porous sheet or other materials are to be added to the barrier material. Again, however, it should be remembered that multiple coats can result in latex layer thickness which may adversely affect the breathability of the overall material.

Finally, additives other than crosslinking agents and rheology modifiers can be incorporated into the aqueous coating solution or film of polymeric latex material, if desired. Such additives include binders, extenders, fillers, pigments, dyes, defoamers, preservatives, fungicides, wetting agents, deodorants, fluorescent agents, and the like.

It may be noted at this point that the porous sheet can be a single layer or a composite of two or more layers. Moreover, the breathable barrier can be a composite of more than the two layers required by the present invention. Composite structures are, in fact, preferred since the use of multiple layers permits one to tailor the breathable barrier for any desired combination of barrier properties, including water vapor transmission rate, durability and aesthetic properties.

By way of illustration of multilayer constructions for the barrier, when the barrier is to be used as the baffle in a sanitary napkin, the barrier can be a composite of a thermally bonded carded web, a second layer as provided by the present invention, and a meltblown web first layer, with the meltblown web being the inner or body side layer. Alternatively, the bonded carded web can be replaced with a spunbonded web.

For disposable diaper or incontinent pad applications, an example of a suitable outer cover is a composite of a first meltblown web as the first layer, two layers of a film as provided by the present invention, a third layer of a film as provided by the present invention to serve as an adhesive for the next layer which is a second meltblown web, and a final layer which is a spunbonded web. Each meltblown web can have a basis weight of, for example, 17 g/m$^2$, and the spunbonded web can have a basis weight of, for example, 23.8 g/m$^2$, with the spunbonded web being the outermost layer to provide increased durability and abrasion resistance since the meltblown webs are often times more fragile. That is, the first meltblown layer is placed next to the absorbent batt within the disposable diaper or incontinent pad. Of course, other constructions are possible and come within the spirit and scope of the present invention.

The present invention is further described by the examples which follow which illustrate certain preferred embodiments. Such examples are not to be construed as in any way limiting either the spirit or scope of the present invention. In the examples, all temperatures are in degrees Celsius and all amounts are in parts by weight, unless indicated otherwise.

In the examples, the water vapor transmission rate was determined in accordance with ASTM Method E 96-80, Standard Test Methods for Water Vapor Transmission of Materials, Procedure 12. The apparatus employed was a Vapometer (Catalog No. 68-1, Thwing-Albert Instrument Company, Philadelphia, Pa.). The apparatus consisted of a two-inch (about 5.1-cm) deep aluminum cup having a flanged top with a neoprene rubber gasket. The inner diameter of the flange was 2.5 inches (about 6.4 cm). About 100 ml of water was added to the cup and a sample of the breathable barrier to be tested was sealed mechanically over the open end of the cup and weighed. The sample-cup assembly was placed in an oven at 37° C. and about 50 percent relative humidity. Periodic weighings of the sample-cup assembly permitted calculation of the water vapor transmission rate (WVTR).

The effectiveness of the coated porous sheet as a barrier to liquid water was measured by INDA Standard Test 80.7-70 (82), INDA Standard Test for Saline Repellency of Nonwovens, often referred to as the Mason Jar Test. The test liquid was 0.9 percent by weight saline solution at a temperature of about 21° C. In both tests, the coated porous sheet was oriented inwardly, i.e., with the porous sheet closest to the saline solution. The latex coated samples according to the present invention were found to be impermeable to the saline solution for at least about one hour at a hydrostatic head of at least about 11.4 cm.

EXAMPLES

Numerous samples of latex coated materials were prepared and evaluated in an effort to determine the efficacy of the material of the present invention. In the previously mentioned exemplary uses, which included personal absorbent products and more durable goods such as rainwear, several key properties were found to be necessary for the breathable barrier material to function well. First, the material must be both breathable and a barrier. A measure of breathability is the water vapor transmission rate (WVTR) of the material. As a point of comparison, film materials such a polyethylene which are commonly used as an outer cover on diapers have very little breathability and thus are a very good barrier to liquids. Conversely, there are materials such as polyvinyl alcohol (PVOH)-coated nonwoven materials which are quite breathable but lack the strong barrier properties of film. Thus, the designing of a breathable barrier material requires the optimization of two properties which tend to compete against one another.

A second important property is durability. Polyethylene films given sufficient film thickness are very durable. They are flexible so they resist cracking and other breaches of their barrier properties at normal temperatures. Films are also fairly abrasion resistant. However, both these advantages come at the expense of comfort. Polyethylene films are hot to wear and they are noisy when flexed—a problem referred to as "rattling" in diaper construction. Polyethylene films can also be washed off and exposed to moderate temperatures without degrading. PVOH-coated nonwovens, on the other hand, while providing superior breathability as compared to polyethylene films, suffer from the standpoint of durability. PVOH is a water-soluble polymer at elevated temperatures. As a result, PVOH coatings can possibly dissolve during washing, thereby destroying the durability of the material. It has also been found that over extended periods of time, PVOH-coated materials will begin to crack and such cracking is enhanced by flexing, which makes the material less effective from a barrier standpoint in longer use goods such as rainwear. Therefore, to determine the properties of the polymeric latex-coated materials of the present invention, numerous samples were prepared and tested relative to their breathability and barrier properties. These samples were also compared to a polyethylene film and a PVOH-coated material to gauge the latex-coated material's performance.

Samples of five composites were prepared and tested. All the composite materials used an identical base of nonwoven material comprising a 0.7 ounce per square yard (OSY) spunbond and a 0.5 OSY meltblown component, both of which were composed of polypropylene fibers and thermally bonded together with approximately a 15% bonding area using a diamond bond pattern. The spunbond layer fibers had an average diameter of 16-35 microns while the average diameter of the meltblown fibers was 1-10 microns. The average pore size diameter of the meltblown layer at its surface opposite the spunbond layer was 5-50 microns. Various types of barrier coatings were applied to the meltblown layer of the base material to produce the composites listed below. Several of the coatings contained additives, the trade name, class and source of which are listed in Table I. Relative portions of the additives are given on a dry-parts basis.

Composite A—coating was a 17 gsm extruded film of EMA/LDPE at a coating thickness of 0.5 mils.

Composite B—coating composition comprised Rhoplex E-940 acrylic latex (100 parts), Zinc Oxide Solution #1 (3 parts) and Rheology Modifier QR 708 urethane polymer/propylene glycol composition (0.002 to 0.157 part) for a single coat total add-on of 19 gsm.

Composite C—two separate coats of coating composition B with a total add-on of 17 gsm.

Composite D—coating composition comprised Rhoplex E-940 acrylic latex (100 parts), FC-461 fluorochemical water repellent (4 parts), XAMA 7 tri-functional aziridine derivative crosslinker (3 parts), ammonium oxalate (0.2 part), and Triton X100 octylphenoxypolyethoxyethanol surfactant (0.5 part) for a total coating add-on of 12 gsm.

Composite E—coating composition comprised Vinol 165 superhydrolyzed polyvinyl alcohol (5 parts) and glycerin (2 parts) for a total add-on of 12 gsm.

The EMA/LDPE of Composite A was extruded onto the exposed side of the meltblown web portion of the base sheet. The latex and PVOH coatings were applied to the meltblown layer of the base sheet in aqueous form using a Meyer rod and then dried.

TABLE I

| TRADE NAME | CLASS | SOURCE |
|---|---|---|
| | CHEMICALS USED | |
| AIRFLEX JF-132 | VINYL-ACETATE/ETHYLENE COPOLYMER EMULSION | AIR PRODUCTS |
| CARBOWAX 200 | POLYETHYLENE GLYCOL | UNION CARBIDE |
| FC-461 | FLUOROCHEMICAL WATER REPELLENT | CIBA GEIGY |
| RHEOLOGY MODIFIER QR-708 | URETHANE POLYMER/PROPYLENE GLYCOL COMPOSITION | ROHM & HAAS |
| RHOPLEX E-940 | ACRYLIC LATEX | ROHM & HAAS |
| TRITON X-100 | OCTYLPHENOXYPOLYETHOXYETHANOL SURFACTANT | ROHM & HAAS |
| VINOL 165 | SUPERHYDROLYZED POLYVINYL ALCOHOL | AIR PRODUCTS |
| XAMA-7 | AZIRIDINE DERIVATIVE, CROSSLINKER | VIRGINIA CHEMICAL CO. |
| ZINC OXIDE SOLUTION #1 | ZINC OXIDE/AMMONIUM CARBONATE CROSSLINKING AGENT | S. C. JOHNSON |

Figure 7:
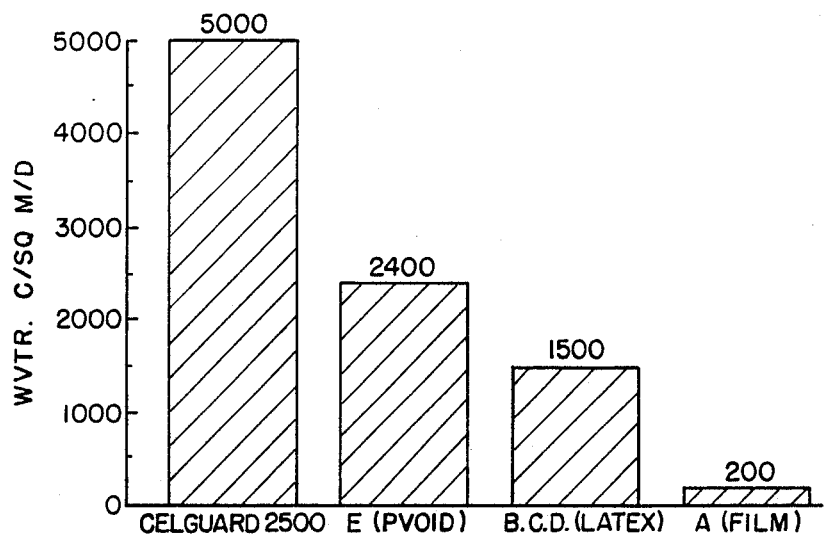
FIG. 7 is a bar graph depicting the water vapor transmission rates of the various samples of breathable barrier materials.

All five composites were subject to testing to determine their respective WVTRs as compared to a standard material, Celguard 2500, which is a microporous film obtained from Celanese. The results of the WVTR testing are presented in graph form in FIG. 7. The Celguard 2500 had a WVTR of 5,000 g/m$^2$/day (24 hours). The highest WVTR of the composites was Composite E (PVOH-12 gsm) with a WVTR of 2,400 g/m$^2$/d. The latex-coated composites B, C and D each had WVTRs of approximately 1,500 g/m$^2$/d, while composite A (Film-17 gsm) had a negligible WVTR of about 200 g/m$^2$/d.

Each of the samples was also subjected to hydrohead test to measure the materials' resistance to water/urine penetration. Under these conditions, a material with larger holes would register a lower hydrohead end point. Composite A (film-17 gsm) had no measurable hydrohead since the end point, if it existed, exceeded the range of the hydrohead tester. The hydrohead data for the other composites is presented in FIG. 9.

Figure 8:
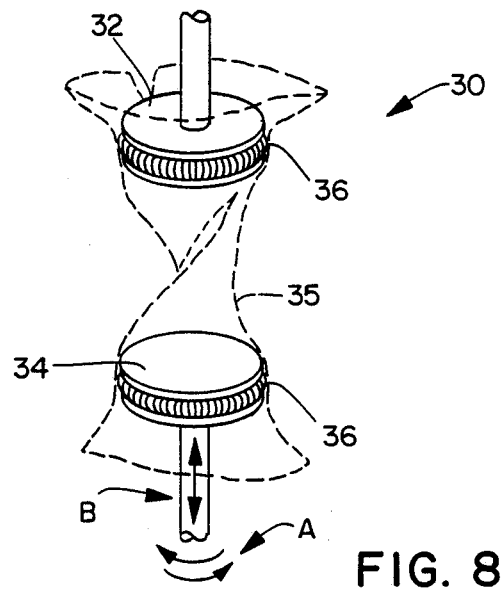
FIG. 8 is a perspective view of the flexing device used to expose the breathable barrier samples to flexing similar to what would be encountered during normal use.

As mentioned at the outset, one of the primary properties a breathable barrier material is durability. Each of the samples of the composites was initially tested before it had been used or subjected to any real flexing. Under normal use conditions, however, such materials can experience high amounts of flexing. As a result, a test apparatus as shown in FIG. 8 was devised to expose the samples to cyclical flexing to simulate in-use wear and tear. After each cycle of flexing the samples were subjected to a hydrohead test to determine whether the barrier properties had been significantly adversely affected. These results are also presented in FIG. 9.

Figure 9:
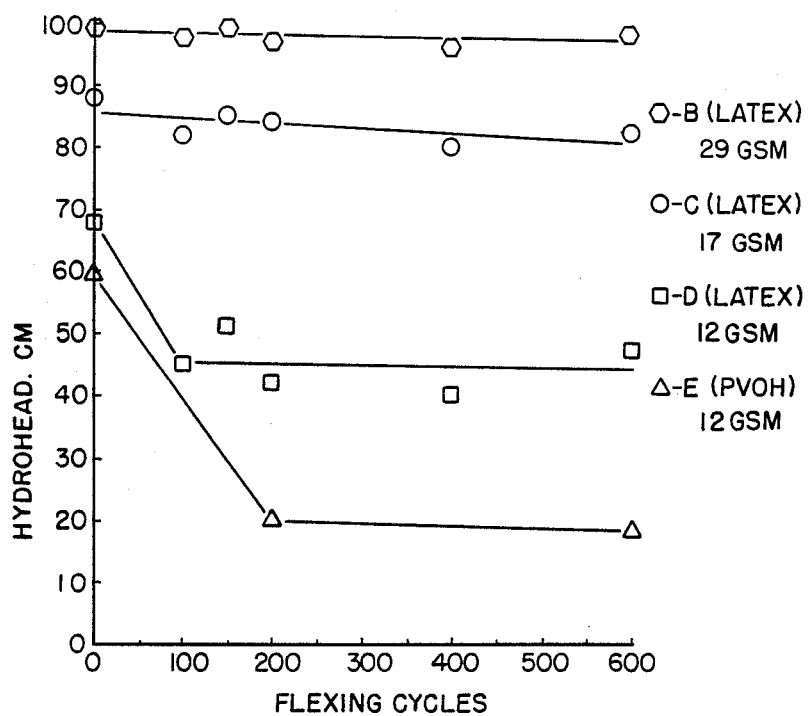
FIG. 9 is a graph depicting the effects of flexing on the hydrohead properties of the breathable barrier materials.

Referring to FIG. 8, to gain the data presented in FIG. 9 each of the samples was placed on a device 30 which includes a fixed disk 32 and a reciprocating disk 34. Each of the samples 35 was held to the disks 32 and 34 by springs 36. The reciprocating disk 34 was then activated and was capable of twisting the sample back and forth (arrows A) and up and down (arrows B) thereby approximating the movements that such materials would be exposed to during normal use.

Each of the samples of the composites B, C D and E was tested under 100, 150, 200, 400, and 600 flexing cycles and the hydroheads were then measured. As can be seen from the data plotted in FIG. 9, Composite A (latex-29 gsm) suffered virtually no reduction in its hydrohead even after 600 flexing cycles. The next best performer was Composite C (latex-17 gsm) followed by Composite D (latex-12 gsm) and lastly, Composite E (PVOH-12 gsm).

In a direct comparison of barrier materials with equal coatings of latex (Composite D-12 gsm) and PVOH (Composite E-12 gsm) it can be seen that, while both materials had dramatic initial drops in their hydroheads, over extended flexing (600 cycles) the latex material was still able to maintain over twice the hydrohead of the PVOH-coated material. From a coating thickness point of view the thicker coated latex materials (Composite C-17 gsm) and Composite B-29 gsm) were better able to maintain their barrier properties over extended flexing cycles. Thus, for optimum barrier properties the coating thickness of the material should be in the range of 17 gsm or higher.

Figure 10:
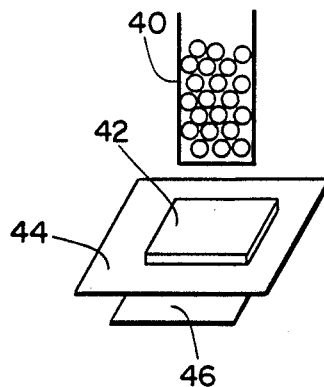
FIG. 10 is a diagrammatic view of the apparatus used to perform the dead weight test on the breathable barrier materials.

To further substantiate the barrier properties of the present invention, samples of the various composites were subjected to a procedure referred to as the dead weight test which is depicted in FIG. 10. The dead weight test is used to predict whether a breathable barrier material when used as an outer cover on a diaper will leak when a baby sits on the wet diaper over an extended period of time. In this test, a dead weight 40 of 2.6 psi is placed on top of a wetted fluff pad 42 which is in turn placed on top of the coated side of a sample composite 44. A preweighed blotter 46 is then placed under the composite 44, adjacent the spunbond material. After two hours the blotter 46 is reweighed to determine any weight gain due to moisture pickup by the blotter 46. Normally the blotter can gain up to about 0.5 g in moisture without being visibly wet. Dead weight measurements were taken before flexing and after 100, 150, 200, 400 and 600 cycles.

Figure 11:
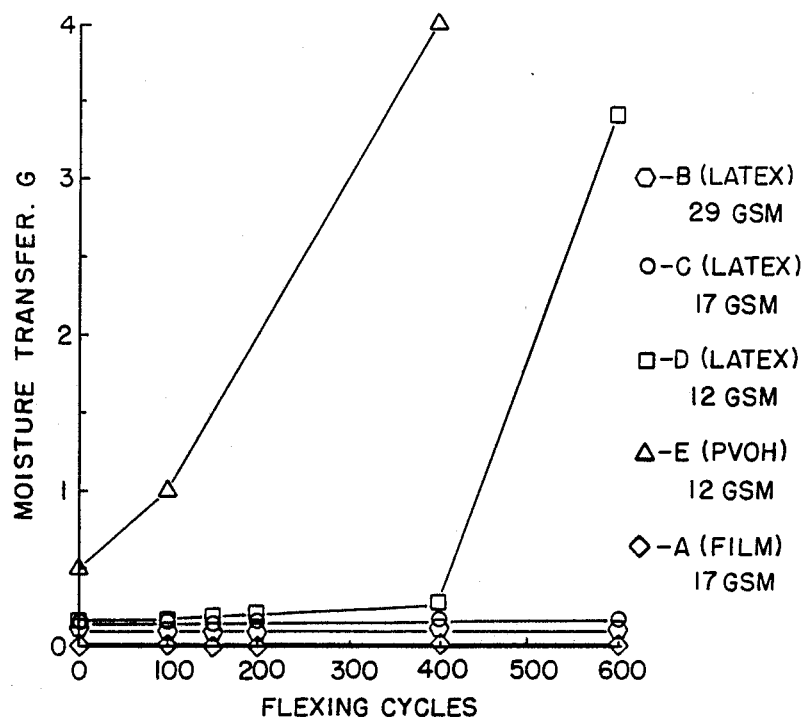
FIG. 11 is a graph depicting the effects of flexing on the moisture transfer properties of the breathable barrier materials determined using the dead weight apparatus depicted in FIG. 10.

Referring to FIG. 11, Composite A (EMA/LDPE film-17 gsm) did not allow any moisture to pass through to the blotter. Composite B (latex-29 gsm) and Composite C (latex-17 gsm) allowed 0.10 g and 0.16 g of moisture vapor to pass through to the blotter respectively after flexing for 600 cycles. Composite D (latex-12 gsm) and Composite E (PVOH-12 gsm) leaked disastrously after flexing for 600 and 400 cycles respectively. Once again, the testing results indicate that the latex coatings were superior to PVOH, especially at coating weights of 17 gsm and above.

Figure 12:
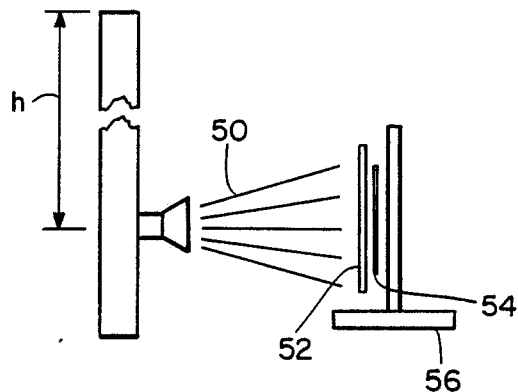
FIG. 12 is a diagrammatic view of the apparatus used to perform the rain test on the breathable barrier materials.

Additional barrier data was generated through a procedure depicted in FIG. 12 and referred to as the Rain Test which is a standard test commonly used in the industry to evaluate rainwear. A stream of water 50 under a constant 122 cm waterhead of pressure at approximately 27° C. is directed horizontally at a vertically suspended sample 52 for a period of four minutes. Positioned behind the sample 52 there is placed a piece of preweighed blotter paper 54 and the sample 52 together with the blotter paper 54 are secured to a holder 56. Upon completion of the test, the blotter paper 54 is reweighed to calculate the amount of moisture which passes through the sample. Composite E (PVOH-12 gsm) leaked disastrously seconds after being exposed to the shower, a possible cause being that the water may have partially dissolved the PVOH, leaving holes behind. All of the other four composites passed the test after an exposure time of four minutes with each allowing less than 0.2 g/m$^2$/24 hrs. of moisture to pass through the samples.

Having thus described the invention in detail, various other modifications and changes can be made by those having ordinary skill in the art without departing from the spirit and scope of the following claims.

What is claimed is:

1. A breathable barrier which comprises:
   A. a first layer which is a porous sheet having a first side and a second side; and
   B. a second layer joined to said first side of said first layer, which second layer comprises a continuous film of a polymeric latex material, in which:
   said film is not microporous in that it is substantially free of voids which connect the two surfaces of said film; and
   said film has an average thickness of from about 10 to about 250 microns;
   wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate at 37° C. and about 50 percent relative humidity of from about 100 to about 2,200 g/m$^2$/24 hours and is impermeable to 0.9 percent by weight saline solution at about 21° C. for a period of at least about one hour at a hydrostatic head of at least about 11.4 cm.

2. The breathable barrier of claim 1, in which said porous sheet is a nonwoven web.

3. The breathable barrier of claim 2, in which said nonwoven web is a meltblown web.

4. The breathable barrier of claim 3, in which said meltblown web is comprised of polyolefin fibers.

5. The breathable barrier of claim 4, in which said polyolefin fibers are polypropylene.

6. The breathable barrier of claim 4, in which said polyolefin fibers are polyethylene.

7. The breathable barrier of claim 3, in which each of at least about 50 percent of the pores at the surface of said first side of said first layer has a cross-sectional area of less than about $3.2 \times 10^{-8}$ m$^2$.

8. The breathable barrier of claim 3, in which essentially none of the pores at the surface of said first side of said first layer has a cross-sectional area in excess of about $3.2 \times 10^{-8}$ m$^2$.

9. A multilayered absorbent article in which at least one layer is the breathable barrier of claim 1.

10. The absorbent article of claim 9, in which said absorbent article is a disposable diaper.

11. The absorbent article of claim 9, in which said absorbent article is a sanitary napkin.

12. The absorbent article of claim 9, in which said absorbent article is an incontinent pad.

13. The absorbent article of claim 9, in which said absorbent article is a nursing pad.

14. An article of clothing in which at least one layer is the breathable barrier of claim 1.

* * * * *

UNITED STATES PATENT AND TRADEMARK OFFICE
CERTIFICATE OF CORRECTION

PATENT NO. : 4,818,600

DATED : April 4, 1989

INVENTOR(S) : Ralph V. Barun, et al

It is certified that error appears in the above-identified patent and that said Letters Patent is hereby corrected as shown below:

Col. 2, line 6, "vaporpermeable" should read --vapor-permeable--.

Col. 17, line 51&52, a breathable barrier" should read
-- porperties of a breathable barrier --

Col. 18, line 3, "B,C D and E" should read -- B, C, D AND E --
line 37, "C-17 gsm) and should read --C-17 gsm and--.

Signed and Sealed this

Ninth Day of March, 1993

Attest:

STEPHEN G. KUNIN

*Attesting Officer*      *Acting Commissioner of Patents and Trademarks*